United States Patent
Wang

(10) Patent No.: US 10,842,836 B2
(45) Date of Patent: Nov. 24, 2020

(54) DIETARY SUPPLEMENT FOR PROMOTING BLOOD CIRCULATION AND BONES AND MUSCLES

(71) Applicant: Lulin Wang, Beijing (CN)

(72) Inventor: Lulin Wang, Beijing (CN)

(73) Assignee: Lulin Wang, Beijing (CN)

( * ) Notice: Subject to any disclaimer, the term of this patent is extended or adjusted under 35 U.S.C. 154(b) by 115 days.

(21) Appl. No.: 16/231,988

(22) Filed: Dec. 25, 2018

(65) Prior Publication Data

US 2020/0197467 A1    Jun. 25, 2020

(51) Int. Cl.

| | |
|---|---|
| A61K 36/25 | (2006.01) |
| A61K 36/232 | (2006.01) |
| A61K 36/286 | (2006.01) |
| A61K 35/62 | (2006.01) |
| A61K 35/618 | (2015.01) |
| A61K 31/045 | (2006.01) |
| A61K 36/344 | (2006.01) |
| A61K 36/284 | (2006.01) |
| A61K 36/346 | (2006.01) |
| A61P 19/00 | (2006.01) |
| A61P 21/00 | (2006.01) |
| A61K 36/65 | (2006.01) |
| A61K 36/236 | (2006.01) |
| A61K 36/69 | (2006.01) |
| A61K 36/8994 | (2006.01) |

(Continued)

(52) U.S. Cl.
CPC .......... *A61K 36/232* (2013.01); *A23L 33/105* (2016.08); *A61K 31/045* (2013.01); *A61K 31/37* (2013.01); *A61K 35/618* (2013.01); *A61K 35/62* (2013.01); *A61K 36/185* (2013.01); *A61K 36/21* (2013.01); *A61K 36/236* (2013.01); *A61K 36/258* (2013.01); *A61K 36/284* (2013.01); *A61K 36/286* (2013.01); *A61K 36/344* (2013.01); *A61K 36/346* (2013.01); *A61K 36/36* (2013.01); *A61K 36/41* (2013.01); *A61K 36/46* (2013.01); *A61K 36/481* (2013.01); *A61K 36/484* (2013.01); *A61K 36/64* (2013.01); *A61K 36/65* (2013.01); *A61K 36/69* (2013.01); *A61K 36/8945* (2013.01); *A61K 36/8994* (2013.01); *A61P 9/00* (2018.01); *A61P 19/00* (2018.01); *A61P 21/00* (2018.01); *A23V 2002/00* (2013.01)

(58) Field of Classification Search
CPC .................................................. A61K 36/25
See application file for complete search history.

(56) References Cited

PUBLICATIONS

English bibliographic information for Xiangyuan, CN 101244162 A, 2008.*

(Continued)

*Primary Examiner* — Rosanne Kosson
(74) *Attorney, Agent, or Firm* — CBM Patent Consulting, LLC

(57) ABSTRACT

A Bone-Strengthening Pill (BSP) as a dietary supplement to improve blood circulation and strengthen bone and muscle is characterized in that it is made from the following raw materials: *Angelica Sinensis, Pseudo-ginseng* and *Carthamus Tinctorius* L. BSP has the following beneficial effects: promoting blood circulation, dredging microcirculatory disturbance, significantly improving the level of human health, improving blood running in bone tissue and muscle tissue, and preventing or repairing microscopic damage of bone, cartilage tissue and muscle tissue.

2 Claims, 4 Drawing Sheets

(51) Int. Cl.
    *A61K 36/8945*     (2006.01)
    *A61K 36/36*     (2006.01)
    *A61K 36/481*     (2006.01)
    *A61K 31/37*     (2006.01)
    *A61K 36/484*     (2006.01)
    *A61K 36/21*     (2006.01)
    *A61K 36/185*     (2006.01)
    *A61K 36/41*     (2006.01)
    *A61K 36/46*     (2006.01)
    *A61K 36/64*     (2006.01)
    *A61P 9/00*     (2006.01)
    *A23L 33/105*     (2016.01)
    *A61K 36/258*     (2006.01)

(56) References Cited

PUBLICATIONS

English bibliographic information for Ling, CN 108324794 A, published Jul. 27, 2018.*

* cited by examiner

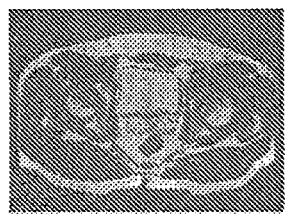
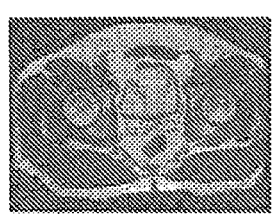
FIG. 2A    FIG. 2B
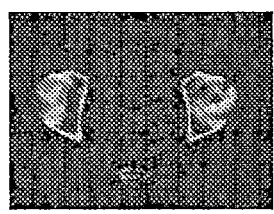
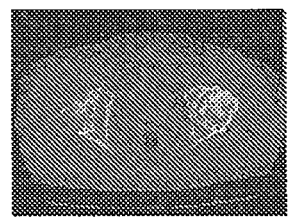
FIG. 3A    FIG. 3B
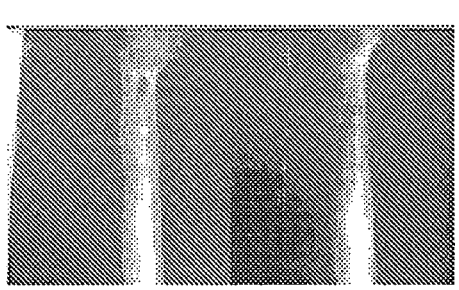
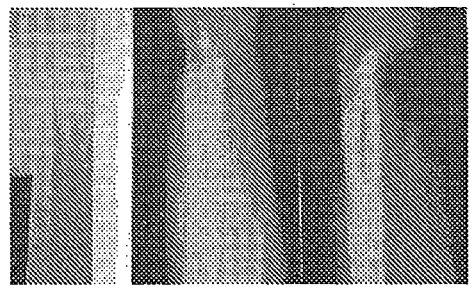
FIG. 4A    FIG. 4B

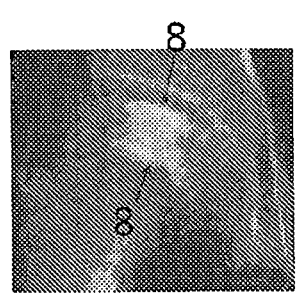 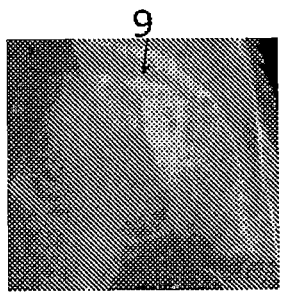 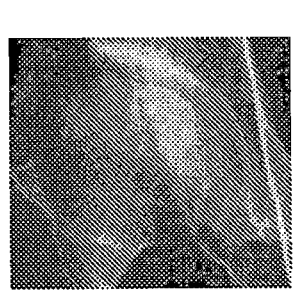
FIG. 5A　　　　　FIG. 5B　　　　　FIG. 5C
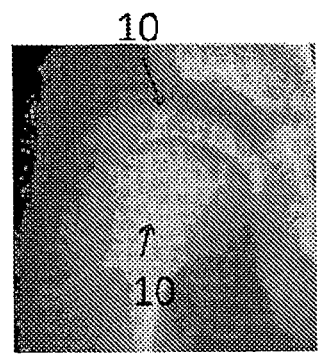 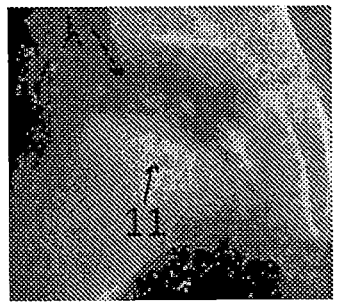 
FIG. 6A　　　　　FIG. 6B　　　　　FIG. 6C
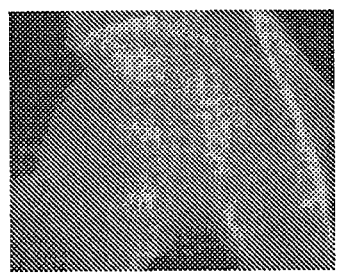 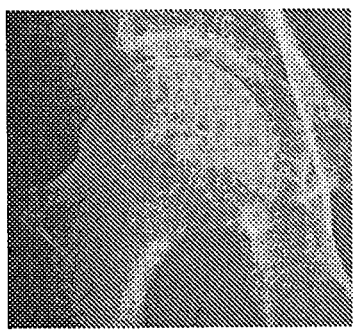
FIG. 7A　　　　　FIG. 7B

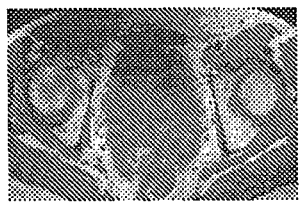
FIG. 8A
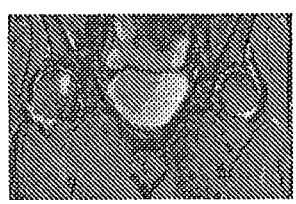
FIG. 8B
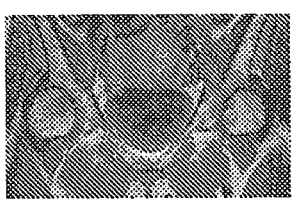
FIG. 8C
FIG. 8D
FIG. 8E
FIG. 8F
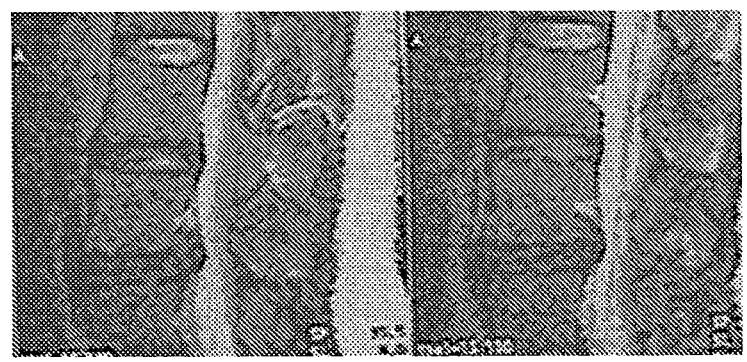
FIG. 9A
FIG. 9B

DIETARY SUPPLEMENT FOR PROMOTING BLOOD CIRCULATION AND BONES AND MUSCLES

FIELD OF THE INVENTION

The present invention relates to a dietary supplement which is made from herbal plants as the main raw materials and has the functions of promoting blood circulation, invigorating health, repairing body damage, especially improving human microcirculation, preventing and repairing damage to bone & cartilage tissue and muscle tissue.

DESCRIPTION OF THE RELATED ART

Blood circulation is the basis for the energy supplement and metabolism of a human body, and a variety of diseases will occur in case of poor blood circulation. Microcirculation, in particular, replenishes the body's material needs through the exchange of substances between blood and tissue fluids. Under normal circumstances, the blood flow of microcirculation is adapted to the metabolic level of tissues and organs, which can ensure the blood flow of tissues and organs and regulate the amount of blood returning to heart. If a microcirculation disorder occurs, it will directly affect the physiological functions of various organs. Microcirculatory disorders can take place in many forms, but more common manifestations mainly include physical weakness and decay of muscle or bone tissue. Among them, physical weakness is mostly manifested as general malaise, shortness of breath, atony, action difficulty, insomnia, irritability, frequent colds, etc., and is mostly accompanied by various degenerative processes. The decay of muscle tissue is often manifested as muscle relaxation, frequent sores, unhealed trauma, etc. The decay of bone tissue is mostly manifested as osteoporosis, susceptibility to fracture, chondritis, osteomyelitis, bone tuberculosis, bone cyst and other kinds of inflammation, especially the weight-bearing parts such as femoral head, which are easily damaged or necrotic due to insufficient blood supply.

In the past, body decay caused by blood circulation disorders, especially the inflammation and injury of bone and muscle tissues, were treated in accordance with pathological changes, and medication or surgical treatment was often used. The duration of medication is long, with an uncertain curative effect. Many medicines should not be taken for a long time as they have toxic and side effects. Surgical treatment usually results in larger trauma, with a high cost, and mostly at the cost of local tissue and function loss. Therefore, it is best to prevent or repair the above symptom of body decay, especially the damage to bone tissue and muscle tissue, by dredging the blood flowing pathway and eliminating the microcirculation obstacle before or at the beginning of its discovery. Obviously, to achieve this, it is necessary to change the existing treatment philosophy and practice, and also to achieve the purpose of promoting blood circulation and removing blood stasis, preventing and repairing micro-obstacles through dietary supplements in daily life. Dietary supplements that can realize this purpose are scarce.

SUMMARY OF THE INVENTION

The purpose of the present invention is to provide a dietary supplement which can dredge blood circulation path, promote microcirculation, prevent or repair microcirculation disturbance, especially strengthen physique, improve and reverse disorders and damage of bone and cartilage tissue and muscle tissue, supplement the nutrients needed to maintain body movement, safeguard the health, normal metabolism and physiological function of bones and muscles, for a human body; and can be taken for a long time as it has no toxic or side effects.

The purpose above is achieved with the following technical scheme: a Bone-Strengthening Pill (BSP) as a dietary supplement to improve blood circulation, strengthen bone and muscle, and promote the repair of bone & cartilage and muscle diseases is provided, characterized in that the dietary supplement is made from the following raw materials: *Angelica sinensis*, *Panax notoginseng* and *Carthamus tinctorius* L.

The ratio of *Angelica sinensis*:*Panax notoginseng*:*Carthamus tinctorius* L. is 280-320: 55-65:12-18 by weight.

Lumbricus, Pearl and Borneol are further included in the raw materials.

Lumbricus, Pearl and Borneol are further included at the ratio of 80-100:2-5:2-5.

*Codonopsis pilosula*, *Rhizoma atractylodis* and *Platycodonopsis grandiflorum* are further included in the raw materials.

*Codonopsis pilosula*, *Rhizoma atractylodis* and *Platycodonopsis grandiflorum* are further included at the ratio of 180-220:55-65:55-65.

Lumbricus, Pearl, Borneol, *Codonopsis pilosula*, *Rhizoma atractylodis* and *Platycodonopsis grandiflorum* are further included in the raw materials.

Lumbricus, Pearl, Borneol, *Codonopsis pilosula*, *Rhizoma atractylodis* and *Platycodonopsis grandiflorum* are further included at the ratio of 80-100:2-5:2-5:180-220:55-65:55-65. *Paeonia lactiflora* Pall, *Ligusticum wallichii*, *Polygala tenuifolia* and *Panax quinquefolius* are further included in the raw materials.

*Paeonia lactiflora* Pall, *Ligusticum wallichii*, *Polygala tenuifolia* and *Panax quinquefolius* are further included at the ratio of 80-100:25-35:25-35:2-5.

Lumbricus, Pearl, Borneol, *Paeonia lactiflora* Pall, *Ligusticum wallichii*, *Polygala tenuifolia* and *Panax quinquefolius* are further included in the raw materials.

Lumbricus, Pearl, Borneol, *Paeonia lactiflora* Pall, *Ligusticum wallichii*, *Polygala tenuifolia* and *Panax quinquefolius* are further included at the ratio of 80-100:2-5:2-5:80-100:25-35:25-35:2-5.

*Atractylodes macrocephala*, *Semen coicis*, *Dioscorea opposita* Thunb and *Pseudostellaria heterophylla* are further included in the raw materials.

*Atractylodes macrocephala*, *Semen coicis*, *Dioscorea opposita* Thunb and *Pseudostellaria heterophylla* are further included at the ratio of 80-100:28-32:28-32:2-5.

Lumbricus, Pearl, Borneol, *Atractylodes macrocephala*, *Semen coicis*, *Dioscorea opposita* Thunb and *Pseudostellaria heterophylla* are further included in the raw materials.

Lumbricus, Pearl, Borneol, *Atractylodes macrocephala*, *Semen coicis*, *Dioscorea opposita* Thunb and *Pseudostellaria heterophylla* are further included at the ratio of 80-100: 2-5:2-5:80-100:28-32:28-32:2-5.

*Astragalus membranaceus*, *Psoralen*, *Polygala tenuifolia* and *Radix glycyrrhizae* are further included in the raw materials.

*Astragalus membranaceus*, *Psoralen*, *Polygala tenuifolia* and *Radix glycyrrhizae* are further included at the ratio of 80-100:28-32:28-32:2-5.

Lumbricus, Pearl, Borneol, *Astragalus membranaceus*, *Psoralen*, *Polygala tenuifolia* and *Radix glycyrrhizae* are further included in the raw materials.

Lumbricus, Pearl, Borneol, *Astragalus membranaceus*, *Psoralen*, *Polygala tenuifolia* and *Radix glycyrrhizae* are further included at the ratio of 80-100:2-5:2-5:80-100:28-32:28-32:2-5.

*Achyranthes bidentata*, Sealwort, *Paeonialactiflora* Pall and *Eurycoma longifolia* are further included in the raw materials.

*Achyranthes bidentata*, Sealwort, *Paeonia lactiflora* Pall and *Eurycoma longifolia* are further included at the ratio of 28-32:28-32: 80-100:2-5.

Lumbricus, Pearl, Borneol, *Achyranthes bidentata*, Sealwort, *Paeonia lactiflora* Pall and *Eurycoma longifolia* are further included in the raw materials.

Lumbricus, Pearl, Borneol, *Achyranthes bidentata*, Sealwort, *Paeonia lactiflora* Pall and *Eurycoma longifolia* are further included at the ratio of 80-100:2-5:2-5:28-32:28-32: 80-100:2-5.

*Ligusticum wallichii*, *Rehmannia glutinosa*, *Eucommia ulmoides* and *Rhodiola rosea* are further included in the raw materials.

*Ligusticum wallichii*, *Rehmannia glutinosa*, *Eucommia ulmoides* and *Rhodiola rosea* are further included at the ratio of 80-100:28-32:28-32:2-5.

Lumbricus, Pearl, Borneol, *Ligusticum wallichii*, *Rehmannia glutinosa*, *Eucommia ulmoides* and *Rhodiola rosea* are further included in the raw materials.

Lumbricus, Pearl, Borneol, *Ligusticum wallichii*, *Rehmannia glutinosa*, *Eucommia ulmoides* and *Rhodiola rosea* are further included at the ratio of 80-100:2-5:2-5:80-100: 28-32:28-32:2-5.

The beneficial effect of the invention is as follows: The dietary supplement described hereof has functions to promote blood circulation, dredge microcirculation disturbance, significantly improve the health level, improve blood running of bone and muscle tissue, prevent or repair microscopic damage to bone & cartilage and muscle tissue of a human body, etc., especially to obviously inhibit or reverse osteoporosis, bone fiber hyperplasia, bone necrosis, chondritis, nonunion, bone tuberculosis, osteomyelitis, bone trauma, osteoarthritis, rheumatoid arthritis, bone cyst and other refractory injury, is non-toxic and free of side effects, can be taken for a long term, and is suitable for all kinds of populations with weak physique, muscle or bone tissue with pathological signs or symptoms.

BRIEF DESCRIPTION OF THE DRAWINGS

FIG. 2A is a NMR image of Embodiment 1 shows large irregularity and uneven signals;

FIG. 2B is 3 NMR image of Embodiment 1 shows uniform signals;

FIG. 3A is a CT image of Embodiment 1 shows unevenly and the necrotic area in the right femoral head;

FIG. 3B is a CT image of Embodiment 1 shows uniform density of the right femoral head;

FIG. 4A is an X-ray image of Embodiment 1 shows the ugger and middle section of the femur 10 had skin ulceration, exudation, and necrosis, and unhealed fistulous tract;

FIG. 4B is an X-ray image of Embodiment 1 shows the dead bone disappeared, the fistulous tract is healed;

FIG. 5A is an X-ray image of Embodiment 2: the arrows (8) indicate the trabecular bone disagpeared in femoral head before treatment;

FIG. 5B is an X-ray image of Embodiment 2: the arrows (9) indicate the trabecular bone in femoral head after treatment;

FIG. 5C is an X-ray image of Embodiment 2 shows normal femoral head after treatment;

FIG. 6A is an X-ray image of Embodiment 3: the arrows (10) indicate coarse surface, increased density, uneven density and epighyseal density in the femoral head;

FIG. 6B is an X-ray image of Embodiment 3: the arrows (11) indicate unclear boundaries, decreased density, and uniform egighyseal density in the femoral head;

FIG. 6C is an X-ray image of Embodiment 3 shows femoral head was slightly flat and had smooth surface, clear trabecular bone and uniform density after treament;

FIG. 7A is an X-ray image of Embodiment 3 shows a large area of decreased density on the right side;

FIG. 7B is an X-ray image of Embodiment 3 shows a normal density on the right side;

FIG. 8A is a NMR image of Embodiment 4 shows the decreased signal on the right femoral head and double-line signs (view 1);

FIG. 8B is a NMR image of Embodiment 4 shows the decreased signal on the right femoral head and double-line signs (view 2);

FIG. 8C is a NMR image of Embodiment 4 shows the decreased signal on the right femoral head and double-line signs (view 3);

FIG. 8D is a NMR image of Embodiment 4 shows the normal signal on the right femoral head and double-line signs (view 1);

FIG. 8E is a NMR image of Embodiment 4 shows the normal signal on the right femoral head and double-line signs (view 2);

FIG. 8F is a NMR image of Embodiment 4 shows the normal signal on the right femoral head and double-line signs (view 3);

FIG. 9A is a NMR image of Embodiment 4 shows fracture and degeneration of the intervertebral cartilage plates of the lumbar spines #4 and 35;

FIG. 9B is a NMR image of Embodiment 4 shows the avulsed intervertebral cartilage plate and vertebral body were repaired, and the intervertebral nerve compression and cutting disappeared after treatment.

DETAILED DESCRIPTION OF THE PREFERRED EMBODIMENT

Figure 1A:
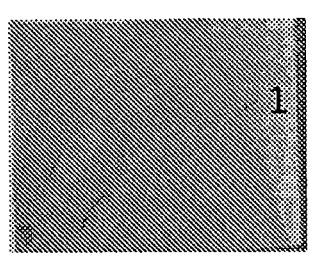
FIG. 1A is an experimental image of Embodiment 1: the arrow (1) indicated smooth surface and chondrocytes arranging in a columnar manner in the femoral head of the normal rats.

Embodiment 1 to produce a dietary supplement that promotes blood circulation and improve bone and muscle. With the experiment name of Bone-Strengthening Pill (BSP), such dietary supplement is made from the following materials: *Angelica sinensis*, *Panax notoginseng* and *Carthamus tinctorius* L.

The raw materials are described as follows:

*Angelica sinensis* is a perennial herb of Family Umbelliferae. Its root is one of the most common traditional Chinese medicines.

*Panax notoginseng* is a perennial herb in the *Panax ginseng* genus of Family Araliaceae of Order Umbellales. Its root is used as medicine. In this study, *Panax notoginseng* is identified to have a role in improving microcirculation.

*Carthamus tinctorius* L., with aliases such as Spinose *Carthamus tinctorius* L., is a herbal plant of Genus *Carthamus tinctorius* L. of Family Compositae, habitually used as traditional Chinese medicine. The study mainly utilizes *Carthamus tinctorius* L.'s functions to promote blood circulation and remove stasis, and to dredge blood microcirculation pathway.

The ratio of *Angelica sinensis:Panax notoginseng:Carthamus tinctorius* L. is 280-320:55-65:12-18 by weight.

The optimal ratio of *Angelica sinensis:Panax notoginseng:Carthamus tinctorius* L. is 300:60:15 by weight.

The dietary supplement mentioned hereof may be processed and taken in a variety of ways. This embodiment only gives two examples:

1. All raw materials are powdered, screened with more 80 meshes, and then made into decoction, powder, pill, tablet or capsule. The usage is to orally take 4-10 g every time, three times a day, for adults.

All raw materials are crushed, decocted in water, and made into decoction or the decoction is concentrated into decoction, powder, pill, tablet and capsule. The usage is to orally take 2-5 g every time, three times a day, for adults.

Safety: The above herbs are all traditional Chinese medicinal materials applicable for long-term use, and safe and non-toxic. The dosage of this embodiment is lower than the limit specified in the relevant classic medical books, so it can be completely identified as being safe. Nevertheless, standard animal experiments and clinical trials have been conducted in this study to prove that the above compatibility of medicines is safe. The following are the experimental results of three applications:

I. Experiment of Weak Population:

Weakness mainly refers to the physical weakness, body discomfort, weakness after illness, postpartum weakness, weakness, shortness of breath, difficulty in walking, insomnia and forgetfulness, etc. caused by poor blood circulation, Since 2010, the multi-parameter microcirculation measuring instrument has been used to detect several physically weak persons for 16 indexes of three categories, such as loop morphology, blood flow state, and surrounding state of nail fold microcirculation. The dietary supplement was taken by those with abnormal indexes. It deemed as recovery that the indexes are improved, the symptoms disappear, and no recurrence is observed after one year of follow-up. Recovery number/Total number×100%=Recovery rate The experimental situations are shown as follows:

| Microcirculation Index | Total Number (Person) | Recovery Number (Person) | Recovery Rate (%) | Average Duration of Medication (Week) |
|---|---|---|---|---|
| Slight Abnormality | 42 | 35 | 83.3 | 3 |
| Moderate Abnormality | 36 | 29 | 80.6 | 5 |
| Severe Abnormality | 32 | 22 | 68.8 | 8 |

It indicates that this product has a good repair and improvement effect on a variety of microcirculation disturbance.

Figure 1B:
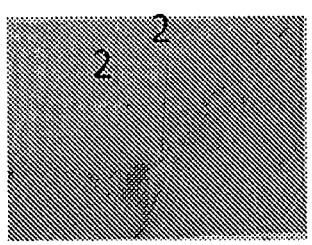
FIG 1B is an experimental image of Embodiment 1: the arrows (2) indicate the femoral head of the model rats has surface necrosis and detachment, collapse and coloboma, and loses chondrocytes.
Figure 1C:
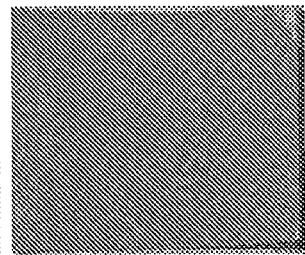
FIG. 1C is an experimental image of Embodiment 1 which shows the femoral head has smooth surfaceI is free of colobomaI and recovered chondrocles in columnar arrangement in the femoral head necrosis when the rats were treated with this product (treatment group)
Figure 1D:
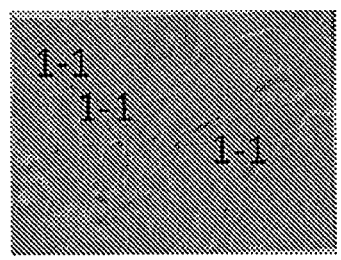
FIG. 1D is an experimental image of Embodiment 1: the arrows (1-1) indicate crimpinessI disorder and fracture of bone trabecula in the model rats.
Figure 1E:
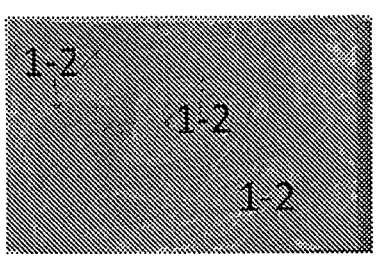
FIG. 1E is an experimental image of Embodiment 1: the arrows (1-2) indicate the focal necrosis of intramedullam cells of femoral head.
Figure 1F:
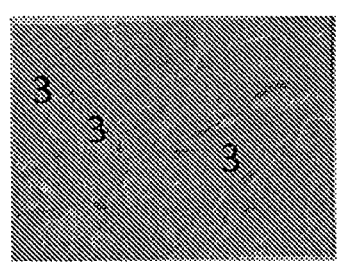
FIG. 1F is an experimental image of Embodiment 1: the arrows 13) indicate rich and morphology in the bone trabecula in the treatment group.
Figure 1G:
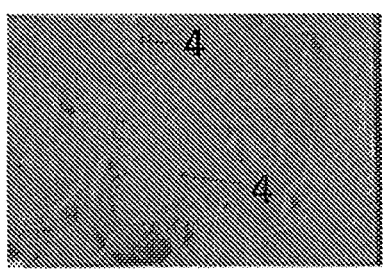
FIG. 1G is an ex erimental ima e of Embodiment 1: the arrows (4) indicate no necrosis in myeloid cells in the treatment group.
Figure 1H:
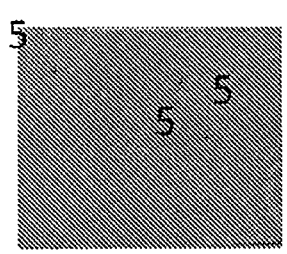
FIG. 1H is an experimental image of Embodiment 1: the arrows (5) indicate a small number of fat particles that were attached to the chondrocyte surface of the normal rat.
Figure 1I:
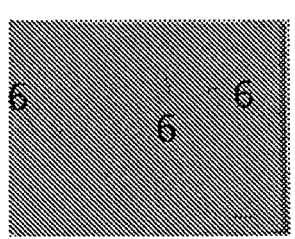
FIG. 1I is an experimental image of Embodiment 1: the arrows (6) indicate a large number of fat particles that were contained in the chondrocytes of femoral head of the model rats.
Figure 1J:
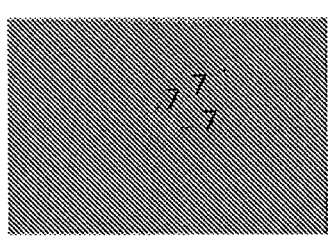
FIG. 1J is an experimental image of Embodiment 1: the arrows (7) indicate a small number of fat particles in the femoral head of the rats in the experimental group.
Figure 1K:
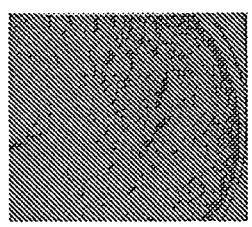
FIG. 1K is an experimental image of Embodiment 1 which shows the capillaries of femoral head of the normal rats are abundantI with clear edges and interweaving into a network to form an "arcuate cup"
Figure 1L:
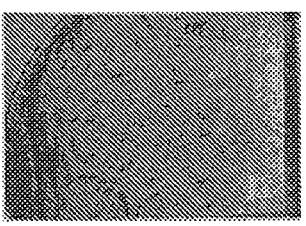
FIG. 1L is an experimental image of Embodiment 1 which shows the capillaries inside the femoral head ofthe model rats were sparse and the "arcuate cup" disappeared.
Figure 1M:
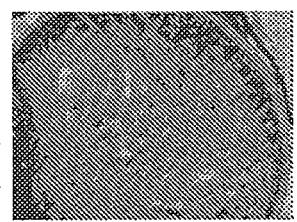
FIG. 1M is an exgerimental image of Embodiment 1 which shows the cagillaries of the femoral head of the rats in the treatment group were significantly increased; with clear edges; and the "arcuate cup" recovered.

II. Experiment of Population with Bone Tissue Injury:

Animal Experiment: Bone density, osteometrics, fat deposition of femoral head, capillary distribution of femoral head and related biochemical indexes were tested and studied with the castrated rat model of osteoporosis and two-legged rat model of ischemic necrosis of femoral head. The experimental results are shown in FIG. 1A-M. In FIG. 1A, the femoral head of the normal rats has smooth surface and chondrocytes arranging in a columnar manner; in FIG. 1B, the femoral head of the model rats has surface necrosis and detachment, collapse and coloboma, and loses chondrocytes; in FIG. 1C, the rats with femoral head necrosis were treated with this product (treatment group) showed that femoral head has smooth surface, is free of coloboma, and recovered chondrocytes in columnar arrangement; in FIG. 1D, the model rats show crimpiness, disorder and fracture of bone trabecula; in FIG. 1E, the model rats show the focal necrosis of intramedullary cells of femoral head; in FIG. 1F., the bone trabecula is rich and morphology is normal in the treatment group; in FIG. 1G, no necrosis was observed in myeloid cells in the treatment group; in FIG. 1H, a small number of fat particles were attached to the chondrocyte surface of the normal rat; in FIG. 1I, a large number of fat particles were contained in the chondrocytes of femoral head of the model rats; in FIG. 1J, a small number of fat particles were observed in the femoral head of the rats in the experimental group; in FIG. 1K, the capillaries of femoral head of the normal rats are abundant, with clear edges and interweaving into a network to form an "arcuate cup"; in FIG. 1L, the capillaries inside the femoral head of the model rats were sparse and the "arcuate cup" disappeared; in FIG. 1M, the capillaries of the femoral head of the rats in the treatment group were significantly increased, with clear edges, and the "arcuate cup" recovered.

The results showed that this product can increase the minimum bone density (MBD), trabecula bone volume (TBV), mean trabecular plate thickness (MTPT) and cortical bone volume (CBV) of the model rats; can significantly increase the mineral appositional rate (MAR) and mean osteoid seam width (MOSW) of the femoral head of the model rats, decrease the fat deposition of the femoral head and enrich capillary distribution of femoral head; and bone-related biochemical tests showed the increased alkaline phosphatase (ALP) and decreased tartrate-resistant acid phosphatase (TRAP). Conclusion: This product can significantly promote bone growth, increase bone density, restore bone substance and blood supply, inhibit and reverse necrotic osteoblasts and chondrocytes, repair bone and cartilage, and is conducive to the recovery of bone and joint diseases and free of any toxic and side effects.

Clinical Trial: Since 2010, this dietary supplement has been taken by many volunteers who were diagnosed by public hospitals. If the bone tissue decay was controlled or repaired, and no recurrence was observed in the two-year follow-up, it was deemed as recovery. Recovery number/Total number×100%=Recovery rate. The experimental conditions are shown as follows:

| Type | Total Number (Person) | Recovery Number (Person) | Recovery Rate (%) | Average Duration of Medication (Week) |
| --- | --- | --- | --- | --- |
| Osteoporosis | 32 | 27 | 84.4 | 20 |
| Osteonecrosis | 36 | 29 | 80.6 | 36 |
| Nonunion of fracture | 32 | 28 | 87.5 | 16 |
| Fibrous dysplasia | 30 | 26 | 86.7 | 34 |
| Bone cyst | 30 | 27 | 90.0 | 30 |
| Chondritis | 34 | 29 | 85.3 | 26 |

It indicates that this product has a good repair and improvement effect on multiple types of bone tissue decay.

Typical Case:

As shown in FIG. 2A-B: A male patient, 37 years old, had been diagnosed with bilateral femoral head necrosis for 3 years, had slight collapse and walking difficulties. He returned to normal work after 12 months of treatment. Before treatment, his MRI image showed abnormal signals of bilateral femoral head, showing large irregularity and uneven signals; abnormal signals of the right femoral head accounted for about 80%, while those of the left for about 60% (FIG. 2A). After treatment, the outline signals of femoral head were uniform, and the abnormal signal area was significantly reduced (FIG. 2B).

As shown in FIG. 3A and B: A male patient, 60 years old, had been diagnosed with bilateral femoral head necrosis for 5 years and was unable to walk. He was cured after 18 months of treatment. Before treatment, his CT image showed that the density of the right femoral head increased unevenly and the necrotic area was about 60%; the left femoral head had fracture, collapse, uneven density and unclear shape, and the necrotic area was about 90% (2-1). After treatment, the density of the right femoral head was uniform and the shape was normal; the shape of the left femoral head was slightly flat, and the density basically returned to being normal (2-2).

III. Experiment of Population with Muscle Tissue Decay:

Muscle tissue decay refers to a variety of abnormalities of muscle tissue caused by poor blood circulation and, such as recurrent muscle sores, unhealed skin wounds, osteomyelitis, and unhealed bone tuberculosis fistula or sinus tract, degenerative arthritis and rheumatoid arthritis.

Since 2010, this dietary supplement has been taken by many volunteers who were diagnosed by public hospitals. If the bone tissue decay was controlled or repaired, and no recurrence was observed in the one-year follow-up, it was deemed as recovery. Recovery number/Total number×100%=Recovery rate.

The experimental results are shown as follows:

| Type | Total Number (Person) | Recovery Number (Person) | Recovery Rate (%) | Average Duration of Treatment (Week) |
| --- | --- | --- | --- | --- |
| Recurrent sores | 34 | 27 | 79.4 | 16 |
| Unhealed wounds | 36 | 30 | 83.3 | 15 |
| Unhealed fistula and fistulous tract | 36 | 31 | 86.1 | 26 |
| Degenerative arthritis | 30 | 24 | 80.0 | 24 |
| Rheumatoid arthritis | 36 | 23 | 63.9 | 36 |

It indicates that this product has a good repair and improvement effect on various types of muscle tissue decay.

Typical Case: As shown in FIG. 4A and B, a male patient, 36 years old, had been diagnosed with left femoral osteomyelitis for 12 years and undergone 3 fractures and 6 surgeries successively. All the upper and middle section of the femur had skin ulceration, exudation, and necrosis, and unhealed fistulous tract. Once pus flowed, he had to lie in bed. The hospital told him to have an amputation. After 7 months of medication, his skin returned to being normal, his dead bone disappeared, his fistulous tract was healed, and he returned to work.

Embodiment 2

Lumbricus, Pearl and Borneol were further included in the raw materials mentioned in Embodiment 1 to form a reinforced formula, with *Angelica sinensis, Panax notoginseng, Carthamus tinctorius* L., Lumbricus, Pearl and Borneol at the ratio of 280-320:55-65:12-18:80-100:2-5:2-5. *Angelica sinensis, Panax notoginseng, Carthamus tinctorius* L., Lumbricus, Pearl and Borneol at the ratio of 300:60:15:90:3:3 are preferred.

Introduction to Newly Further Included Raw Materials:

Lumbricus also known as Earthworm, is a representative animal in Class Oligochaeta in Phylum Annelida and one of the important traditional Chinese medicinal materials. It is a nutrient source integrating protein, vitamins, minerals and enzymes.

Peal (Pernulo) is a shiny particle formed in pearl sacs of several pearly shellfishes. It is a nutrient source integrating minerals, amino acids and nutrients.

Borneol, a natural crystalline compound precipitated from the resin of Kapur trees of Dipterocarpaceae plants.

The processing and taking methods, safety, and experimental method of the Bone-Strengthening Pill (BSP) as a dietary supplement are the same as those of Embodiment 1:

The following are the experimental results of three applications:

I. The experimental situations of the weak population are as follows:

| Microcirculation Index | Total Number (Person) | Recovery Number (Person) | Recovery Rate (%) | Average Duration of Medication (Week) |
|---|---|---|---|---|
| Slight Abnormality | 46 | 40 | 87.0 | 3 |
| Moderate Abnormality | 36 | 30 | 83.3 | 5 |
| Severe Abnormality | 32 | 25 | 78.1 | 8 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 36 | 31 | 86.1 | 18 |
| Osteonecrosis | 34 | 29 | 85.3 | 32 |
| Nonunion of fracture | 30 | 27 | 90.0 | 14 |
| Fibrous dysplasia | 32 | 28 | 87.5 | 32 |
| Bone cyst | 36 | 32 | 88.9 | 30 |
| Chondritis | 30 | 26 | 86.7 | 25 |

It indicates that this product has a good repair and improvement effect on multiple types of bone tissue decay, which is superior to that of Embodiment 1.

Typical Case:
As shown in FIG. 5A-C, a 29-year-old male patient had alcoholism. Before treatment, his femoral head had collapsed and deformation and uneven density, and the trabecular bone disappeared (FIG. 5A). There was a significant improvement after treatment (FIG. 5B). After treatment, the femoral head looked the same as before, but bone density was uniform, and the patient returned to work (FIG. 5C).

III. The experimental results of the population with muscle tissue decay are shown in the following table:

| Type | Total Number (Person) | Recovery Number (Person) | Overall Response Rate (ORR) (%) | Average Duration of Medication (Week) |
|---|---|---|---|---|
| Recurrent sores | 38 | 32 | 84.2 | 14 |
| Unhealed wounds | 32 | 29 | 90.6 | 14 |
| Unhealed fistula and fistulous tract | 36 | 33 | 91.7 | 24 |
| Degenerative arthritis | 32 | 28 | 87.5 | 22 |
| Rheumatoid arthritis | 36 | 24 | 66.7 | 34 |

It indicates that this product has a good repair and improvement effect on various types of muscle tissue decay.

Embodiment 3

*Codonopsis pilosula*, *Rhizoma atractylodis* and *Platycodonopsis grandiflorum* are further included in the raw materials mentioned in Embodiment 1 to form a reinforced formula, with *Angelica sinensis*, *Panax notoginseng*, *Carthamus tinctorius* L., *Codonopsis pilosula*, *Rhizoma atractylodis* and *Platycodonopsis grandiflorum* at the ratio of 280-320:55-65:12-18:180-220:55-65:55-65. *Angelica sinensis*, *Panax notoginseng*, *Carthamus tinctorius* L., *Codonopsis pilosula*, *Rhizoma atractylodis* and *Platycodonopsis grandiflorum* at the ratio of 300:60:15:200:60:60 are preferred.

Introduction to Newly Further Included Raw Materials:
*Codonopsis pilosula* (*Codonopsis pilosula* (Franch.) Nannf. for scientific name), is a perennial herb of Genus *Codonopsis* of Family Campanulaceae.

*Rhizoma atractylodis* (*Atractylodes lancea* (Thunb.) DC. for scientific name) is a perennial herb of Genus *Atractylodes* of Family Compositae.

*Platycodonopsis grandiflorum* (*Platycodon grandiflorus* for scientific name), with alias such as Package Flower, Bell Flower and Mitral Flower, is a perennial herb whose root can be used as medicine.

The processing and taking methods, safety, and experimental method of the dietary supplement described herein are the same as those of Embodiment 1:

The following are the experimental results of three applications:

I. The experimental situations of the weak population are as follows:

| Microcirculation Index | Total Number (Person) | Recovery Number (Person) | Recovery Rate (%) | Average Duration of Medication (Week) |
|---|---|---|---|---|
| Slight Abnormality | 44 | 40 | 90.9 | 3 |
| Moderate Abnormality | 36 | 31 | 86.1 | 5 |
| Severe Abnormality | 34 | 29 | 85.3 | 8 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 32 | 28 | 87.5 | 17 |
| Osteonecrosis | 32 | 27 | 84.4 | 30 |
| Nonunion of fracture | 32 | 29 | 90.6 | 13 |
| Fibrous dysplasia | 34 | 29 | 85.3 | 30 |
| Bone cyst | 32 | 28 | 87.5 | 29 |
| Chondritis | 33 | 29 | 87.9 | 25 |

It indicates that this product has a good repair and improvement effect on multiple types of bone tissue decay.

Typical Case:
As shown in FIG. 6A-C, a female patient, 9 years old, has been sick for 2 years and recovered after 16 months of medication. Before treatment, her femoral head had coarse surface, increased density, uneven density and epiphyseal density (FIG. 6A). After 7 months of treatment, her femoral head had unclear boundaries, decreased density, and uniform epiphyseal density (FIG. 6B). After treatment, her femoral head was slightly flat and had smooth surface, clear trabecular bone and uniform density (FIG. 6C).

As shown in FIG. 7A and B, a patient, 45 years old, had a large area of decreased density on the right side according to the X-ray image, and recovered after taking the medicine.

III. The experimental results of the population with muscle tissue decay are shown in the following table:

| Type | Total Number (Person) | Recovery Number (Person) | Overall Response Rate (ORR) (%) | Average Duration of Medication (Week) |
| --- | --- | --- | --- | --- |
| Recurrent sores | 32 | 28 | 87.5 | 14 |
| Unhealed wounds | 36 | 34 | 94.4 | 14 |
| Unhealed fistula and fistulous tract | 32 | 30 | 93.8 | 22 |
| Degenerative arthritis | 34 | 29 | 85.3 | 22 |
| Rheumatoid arthritis | 36 | 25 | 69.4 | 32 |

It indicates that this product has a good repair and improvement effect on various types of muscle tissue decay, which is superior to that of Embodiment 1.

Embodiment 4

Lumbricus, Pearl, Borneol, *Codonopsis pilosula*, *Rhizoma atractylodis* and *Platycodonopsis grandiflorum* are further included in the raw materials mentioned in Embodiment 1 to form a reinforced formula, with *Angelica sinensis*, *Panax notoginseng*, *Carthamus tinctorius* L., Lumbricus, Pearl, Borneol, *Codonopsis pilosula*, *Rhizoma atractylodis* and *Platycodonopsis grandiflorum* at the ratio of 280-320: 55-65:12-18:80-100:2-5:2-5:180-220:55-65:55-65.

The optimal ratio of *Angelica sinensis*:*Panax notoginseng*:*Carthamus tinctorius* L.:Lumbricus:Pearl:Borneol:*Codonopsis pilosula*:*Rhizoma atractylodis*:*Platycodonopsis grandiflorum* is 300:60:15:90:3:3:200:60:60 by weight.

The processing method of the dietary supplement mentioned herein is to powder all raw materials, screen the powder with more 80 meshes, and then made into decoction, powder, pill, tablet or capsule.

The usage of the dietary supplement is to orally take 5-12 g every time, three times a day, for adults.

The processing method of the dietary supplement mentioned herein is to crush all raw materials, decoct them in water, and make into decoction or concentrate the decoction into decoction, powder, pill, tablet or capsule.

The usage of the dietary supplement is to orally take 3-6 g every time, three times a day, for adults.

The experimental method is the same as that Embodiment 1. The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
| --- | --- | --- | --- | --- |
| Slight Abnormality | 43 | 40 | 93.0 | 3 |
| Moderate Abnormality | 33 | 29 | 87.9 | 5 |
| Severe Abnormality | 36 | 31 | 86.1 | 8 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
| --- | --- | --- | --- | --- |
| Osteoporosis | 34 | 30 | 88.2 | 16 |
| Osteonecrosis | 36 | 32 | 88.9 | 30 |
| Nonunion of fracture | 32 | 30 | 93.8 | 12 |
| Fibrous dysplasia | 36 | 32 | 88.9 | 28 |
| Bone cyst | 36 | 33 | 91.7 | 27 |
| Chondritis | 30 | 27 | 90.0 | 20 |

It indicates that this product has a good repair and improvement effect on multiple types of bone tissue decay.

Typical Case:

As shown in FIG. 8A-F, a patient, 59 years old, had the decreased signal on the right femoral head and double-line signs (FIG. 8A-C) before treatment. The signal returned to normal after treatment (FIG. 8D-F).

As shown in FIG. 9A and B, a patient, 38 years old, had lumbar sprain, vertebral cartilage avulsion, intervertebral disc herniation, and low back pain with pain in both lower limbs, and was unable to get out of bed or move. He was cured after three months of treatment. Before treatment, the MRI image showed fracture and degeneration of the intervertebral cartilage plates of the lumbar spines #4 and 35, vertebral body avulsion at the ligamentous attachment, intervertebral disc protrusion to the spinal canal, and obvious compression of the nerves in the spinal canal (A). After treatment, the avulsed intervertebral cartilage plate and vertebral body were repaired, and the intervertebral nerve compression and cutting disappeared (B).

III. The experimental results of the population with muscle tissue decay are shown in the following table:

| Type | Total Number (Person) | Recovery Number (Person) | Recovery Rate (%) | Average Duration of Medication (Week) |
| --- | --- | --- | --- | --- |
| Recurrent sores | 36 | 33 | 91.7 | 13 |
| Unhealed wounds | 38 | 36 | 94.7 | 12 |
| Unhealed fistula and fistulous tract | 32 | 30 | 93.8 | 20 |
| Degenerative arthritis | 30 | 27 | 90.0 | 20 |
| Rheumatoid arthritis | 36 | 26 | 72.2 | 30 |

It indicates that this product has a good repair and improvement effect on various types of muscle tissue decay.

Embodiment 5

*Paeonia lactiflora* Pall, *Ligusticum wallichii*, *Polygala tenuifolia* and *Panax quinquefolius* are further included in the raw materials *Angelica sinensis*, *Panax notoginseng* and *Carthamus tinctorius* L. to form a reinforced formula, with *Angelica sinensis*, *Panax notoginseng*, *Carthamus tinctorius* L., *Paeonia lactiflora* Pall, *Ligusticum wallichii*, *Polygala tenuifolia* and *Panax quinquefolius* at the ratio of 280-320: 55-65:12-18:80-100:25-35:25-35:2-5.

*Angelica sinensis*, *Panax notoginseng*, *Carthamus tinctorius* L., *Paeonia lactiflora* Pall, *Ligusticum wallichii*,

*Polygala tenuifolia* and *Panax quinquefolius* at the ratio of 300:60:15:90:30:30:3 are preferred.

Introduction to Newly Further Included Raw Materials:

*Paeonia lactiflora* Pall is dry root of *Paeonia tactilora* Pall., a Ranunculaceae plant.

*Ligusticum wallichii* (Scientific name: *Ligusticum chuanxiong* Hort) is a herbal plant for traditional Chinese medicine.

*Polygala tenuifolia* (Scientific name: *Polygala tenuifolia* Willd), also known as Fine Grass and Line Tea, is a perennial herb. Traditional Chinese medicine believes that *Polygala tenuifolia* has the functions of tranquilizing mind, promoting intelligence, and relieving sputum and swelling. This application is based on the close relationship between human microcirculation and e regulation of the nervous system, so *Polygala tenuifolia* is used.

*Panax quinquefolius* (Scientific name: *Panax quinquefolius*) is a perennial plant of Genus *Panax* of Family Araliaceae.

The processing and taking methods, safety and experimental method of the dietary supplement mentioned herein are the same as those of Embodiment 4.

The following are the experimental results of three applications:

I. The experimental situations of the weak population are shown in the following table:

| Microcirculation Index | Total Number (Person) | Recovery Number (Person) | Overall Response Rate (ORR) (%) | Average Duration of Medication (Week) |
|---|---|---|---|---|
| Slight Abnormality | 45 | 42 | 93.3 | 2 |
| Moderate Abnormality | 34 | 30 | 88.2 | 4 |
| Severe Abnormality | 36 | 31 | 86.1 | 7 |

It indicates that this product has a good repair and improvement effect on a variety of microcirculation disturbance, and the time to response is significantly shortened.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 36 | 31 | 86.1 | 14 |
| Osteonecrosis | 32 | 28 | 87.5 | 28 |
| Nonunion of fracture | 36 | 34 | 94.4 | 10 |
| Fibrous dysplasia | 32 | 28 | 87.5 | 26 |
| Bone cyst | 34 | 31 | 91.2 | 26 |
| Chondritis | 36 | 32 | 88.9 | 18 |

It indicates that this product has a good repair and improvement effect on multiple types of bone tissue decay, which is superior to that of Embodiment 1.

III. The experimental results of the population with muscle tissue decay are shown in the following table:

| Type | Total Number (Person) | Recovery Number (Person) | Recovery (%) | Average Duration of Medication (Week) |
|---|---|---|---|---|
| Recurrent sores | 36 | 31 | 86.1 | 13 |
| Unhealed wounds | 36 | 33 | 91.7 | 6 |
| Unhealed fistula and fistulous tract | 36 | 34 | 94.4 | 18 |
| Degenerative arthritis | 32 | 29 | 90.6 | 18 |
| Rheumatoid arthritis | 36 | 28 | 77.8 | 28 |

It indicates that this product has a good repair and improvement effect on various types of muscle tissue decay.

Embodiment 6

Lumbricus, Pearl, Borneol, *Paeonia lactiflora* Pall, *Ligusticum wallichii*, *Polygala tenuifolia* and *Panax quinquefolius* are further included in the raw materials form a reinforced formula, with *Angelica sinensis*, *Panax notoginseng*, *Carthamus tinctorius* L., Lumbricus, Pearl, Borneol, *Paeonia lactiflora* Pall, *Ligusticum wallichii*, *Polygala tenuifolia* and *Panax quinquefolius* at the ratio of 280-320:55-65:12-18:80-100:2-5:2-5:80-100:25-35:25-35:2-5. *Angelica sinensis*, *Panax notoginseng*, *Carthamus tinctorius* L., Lumbricus, Pearl, Borneol, *Paeonia lactiflora* Pall, *Ligusticum wallichii*, *Polygala tenuifolia* and *Panax quinquefolius* at the ratio of 300:60:15:90:3:3:90:30:30:3 are preferred.

The processing and taking methods, safety and experimental method of the dietary supplement described herein are the same as those of Embodiment 4:

The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
|---|---|---|---|---|
| Slight Abnormality | 44 | 42 | 95.5 | 2 |
| Moderate Abnormality | 36 | 33 | 91.7 | 4 |
| Severe Abnormality | 32 | 30 | 93.8 | 7 |

It indicates that this product has a good repair and improvement effect on a variety of microcirculation disturbance, and the time to response is significantly shortened.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 36 | 32 | 88.9 | 12 |
| Osteonecrosis | 36 | 31 | 86.1 | 26 |
| Nonunion of fracture | 32 | 31 | 96.6 | 9 |
| Fibrous dysplasia | 32 | 30 | 93.8 | 24 |
| Bone cyst | 36 | 33 | 91.7 | 24 |
| Chondritis | 32 | 29 | 90.6 | 16 |

It indicates that this product has a good repair and improvement effect on multiple types of bone tissue decay, which is superior to that of Embodiment 1.

III. The experimental results of the population with muscle tissue decay are shown in the following table:

| Type | Total Number (Person) | Recovery Number (Person) | Recovery Rate (%) | Average Duration of Medication (Week) |
| --- | --- | --- | --- | --- |
| Recurrent sores | 36 | 34 | 94.4 | 12 |
| Unhealed wounds | 36 | 35 | 97.2 | 3 |
| Unhealed fistula and fistulous tract | 32 | 31 | 96.9 | 18 |
| Degenerative arthritis | 32 | 29 | 90.6 | 16 |
| Rheumatoid arthritis | 36 | 29 | 80.6 | 26 |

It indicates that this product has a good repair and improvement effect on various types of muscle tissue decay.

Embodiment 7

*Atractylodes macrocephala*, *Semen coicis*, *Dioscorea opposita* Thunb and *Pseudostellaria heterophylla* are further included in the raw materials *Angelica sinensis*, *Panax notoginseng*, and *Carthamus tinctorius* L., to form a reinforced formula, with *Angelica sinensis*, *Panax notoginseng*, *Carthamus tinctorius* L., *Atractylodes macrocephala*, *Semen coicis*, *Dioscorea opposita* Thunb and *Pseudostellaria heterophylla* at the ratio of 280-320:55-65:12-18:80-100:28-32:28-32:2-5.

*Angelica sinensis*, *Panax notoginseng*, *Carthamus tinctorius* L., *Atractylodes macrocephala*, *Semen coicis*, *Dioscorea opposita* Thunb and 3 *Pseudostellaria heterophylla* at the ratio of 300:60:15:90:30:30:3 are preferred.

Introduction to Newly Further Included Raw Materials:
*Atractylodes macrocephala*, with aliases such as Raft Thistle, Winter *Atractylodes macrocephala*, Yang beam, Poplar Raft, is a perennial herb in Genus *Atractylodes* in Family Composite. Its rhizome is used as medicine.

*Semen coicis* (Coix chinensisTod.), also known as Seed of Job's Tears seed and Six Millet Seed, is seed of Coix, a plant of Family Grass.

*Dioscorea opposita* Thunb, also known as Common Yam Rhizome, Rhizome of Common Yam, Dioscoreae rhizome, Yam, Roachster, and White Yam, is dry rhizome of *Dioscorea opposita* Thunb, a plant of Family Dioscoreaceae.

*Pseudostellaria heterophylla*, *Pseudostellaria heterophylla* (Miq) Pax for scientific name, belongs to Genus *Pseudostellaria* in Family Caryophyllaceae (*Pseudostellaria heterophylla* (Miq) Pax ex Pax et Hoffm). Its root is used as medicine.

The processing and taking methods, safety and experimental method of the dietary supplement mentioned herein are the same as those of Embodiment 4.
The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
| --- | --- | --- | --- | --- |
| Slight Abnormality | 50 | 48 | 96.0 | 2 |
| Moderate Abnormality | 36 | 34 | 94.4 | 4 |
| Severe Abnormality | 32 | 28 | 87.5 | 7 |

It indicates that this product has a good repair and improvement effect on a variety of microcirculation disturbance and the time to response is significantly shortened.

II. The experimental results of the population with bone tissue injury are shown in the following table:

| Type | Total Number (Person) | Recovery Number (Person) | Recovery Rate (%) | Average Duration of Medication (Week) |
| --- | --- | --- | --- | --- |
| Osteoporosis | 36 | 32 | 88.9 | 14 |
| Osteonecrosis | 32 | 28 | 87.5 | 28 |
| Nonunion of fracture | 42 | 40 | 95.2 | 10 |
| Fibrous dysplasia | 36 | 32 | 88.9 | 26 |
| Bone cyst | 34 | 31 | 91.2 | 26 |
| Chondritis | 32 | 29 | 90.6 | 18 |

It indicates that this product has a good repair and improvement effect on multiple types of bone tissue decay, which is superior to that of the previous embodiments.

III. The experimental results of the population with muscle tissue decay are shown in the following table:

| Type | Total Number (Person) | Recovery Number (Person) | Recovery Rate (%) | Average Duration of Medication (Week) |
| --- | --- | --- | --- | --- |
| Recurrent sores | 36 | 32 | 88.9 | 13 |
| Unhealed wounds | 32 | 30 | 93.8 | 6 |
| Unhealed fistula and fistulous tract | 32 | 31 | 96.9 | 18 |
| Degenerative arthritis | 36 | 33 | 91.7 | 18 |
| Rheumatoid arthritis | 36 | 29 | 80.6 | 28 |

It indicates that this product has a good repair and improvement effect on various types of muscle tissue decay.

Embodiment 8

Lumbricus, Pearl, Borneol, *Atractylodes macrocephala*, *Semen coicis*, *Dioscorea opposita* Thunb and *Pseudostellaria heterophylla* are further included to the raw materials, form a form a reinforced formula, with *Angelica sinensis*, *Panax notoginseng*, *Carthamus tinctorius* L., Lumbricus, Pearl, Borneol, *Atractylodes macrocephala*, *Semen coicis*, *Dioscorea opposita* Thunb and *Pseudostellaria heterophylla* at the ratio of 180-220:55-65:12-18:80-100:2-5:2-5:80-100:28-32:28-32:2-5.

*Angelica sinensis*, *Panax notoginseng*, *Carthamus tinctorius* L., Lumbricus, Pearl, Borneol, *Atractylodes macrocephala*, *Semen coicis*, *Dioscorea opposita* Thunb and *Pseudostellaria heterophylla* at the ratio of 200:60:15:90:3:3:90:30:30:3 are preferred.

The processing and taking methods, safety and experimental method of the dietary supplement mentioned herein are the same as those of Embodiment 4. The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
|---|---|---|---|---|
| Slight Abnormality | 56 | 54 | 96.4 | 2 |
| Moderate Abnormality | 42 | 40 | 95.2 | 4 |
| Severe Abnormality | 32 | 29 | 90.6 | 7 |

It indicates that this product has a good repair and improvement effect on a variety of microcirculation disturbance, and the time to response is significantly shortened.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 36 | 33 | 91.6 | 14 |
| Osteonecrosis | 32 | 29 | 90.6 | 28 |
| Nonunion of fracture | 43 | 42 | 97.7 | 10 |
| Fibrous dysplasia | 36 | 33 | 91.6 | 26 |
| Bone cyst | 36 | 33 | 91.6 | 26 |
| Chondritis | 38 | 35 | 92.1 | 18 |

It indicates that this product has a good repair and improvement effect on multiple types of bone tissue decay, which is superior to that of the previous embodiments.

III. The experimental results of the population with muscle tissue decay are shown in the following table:

| Type | Total Number (Person) | Recovery Number (Person) | Recovery Rate (%) | Average Duration of Medication (Week) |
|---|---|---|---|---|
| Recurrent sores | 38 | 35 | 92.1 | 13 |
| Unhealed wounds | 32 | 31 | 96.9 | 6 |
| Unhealed fistula and fistulous tract | 36 | 35 | 97.2 | 18 |
| Degenerative arthritis | 36 | 33 | 91.7 | 18 |
| Rheumatoid arthritis | 36 | 30 | 83.3 | 28 |

It indicates that this product has a good repair and improvement effect on various types of muscle tissue decay.

Embodiment 9

*Astragalus membranaceus, Psoralen, Polygala tenuifolia* and *Radix glycyrrhizae* are further included to the raw materials *Angelica sinensis, Panax notoginseng* and *Carthamus tinctorius* L., to form a reinforced formula, with *Angelica sinensis, Panax notoginseng, Carthamus tinctorius* L., *Astragalus membranaceus, Psoralen, Polygala tenuifolia* and *Radix glycyrrhizae* at the ratio of 180-220:55-65:12-18:80-100:28-32:28-32:2-5.

*Angelica sinensis, Panax notoginseng, Carthamus tinctorius* L., *Astragalus membranaceus, Psoralen, Polygala tenuifolia* and *Radix glycyrrhizae* at the ratio of 200:60:15:90:30:30:3 are preferred Introduction to Newly Further Included Raw Materials:

*Astragalus membranaceus* (*Stragalus membranaceus* (Fisch.) Bunge.), also known as *Radix astragali*, is a perennial herb of Genus *Astragalus* of Order Rosaceae of Family Leguminosae.

Psoralea (Scientific name: *Psoralea corylifolia* Linn.), also known as *Fructus psoraleae*, is an annual erect herb of Order Rosaceae of Family Leguminosae. Its fruit is used as medicine.

*Radix glycyrrhizae* (Scientific name: *Glycyrrhiza uralensis* Fisch), also known as Sweet Grass and Sweet Root, is a perennial herb of Order *Glycyrrhiza* of Family Leguminosae.

The processing and taking methods, safety and experimental method of the dietary supplement mentioned herein are the same as those of Embodiment 4.

The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
|---|---|---|---|---|
| Slight Abnormality | 65 | 61 | 93.8 | 2 |
| Moderate Abnormality | 54 | 49 | 90.7 | 4 |
| Severe Abnormality | 36 | 32 | 88.9 | 7 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 38 | 34 | 89.5 | 14 |
| Osteonecrosis | 36 | 32 | 88.9 | 28 |
| Nonunion of fracture | 39 | 38 | 97.4 | 10 |
| Fibrous dysplasia | 36 | 33 | 91.7 | 26 |
| Bone cyst | 38 | 35 | 92.1 | 26 |
| Chondritis | 36 | 33 | 91.7 | 18 |

It indicates that this product has a good repair and improvement effect on multiple types of bone tissue decay, which is superior to that of Embodiment 1.

III. The experimental results of the population with muscle tissue decay are shown in the following table:

| Type | Total Number (Person) | Recovery Number (Person) | Recovery Rate (%) | Average Duration of Medication (Week) |
|---|---|---|---|---|
| Recurrent sores | 46 | 41 | 89.1 | 13 |
| Unhealed wounds | 42 | 39 | 92.9 | 6 |
| Unhealed fistula and fistulous tract | 44 | 42 | 95.5 | 18 |
| Degenerative arthritis | 36 | 33 | 91.7 | 18 |
| Rheumatoid arthritis | 46 | 41 | 89.1 | 28 |

It indicates that this product has a good repair and improvement effect on various types of muscle tissue decay.

Embodiment 10

Lumbricus, Pearl, Borneol, *Astragalus membranaceus, Psoralen, Polygala tenuifolia* and *Radix glycyrrhizae* are further included in the raw materials *Angelica sinensis, Panax notoginseng* and *Carthamus tinctorius* L., to a form a reinforced formula, with *Angelica sinensis, Panax notoginseng, Carthamus tinctorius* L., Lumbricus, Pearl, Borneol, *Astragalus membranaceus, Psoralen, Polygala tenuifolia* and *Radix glycyrrhizae* at the ratio of 180-220:55-65: 12-18:80-100:2-5:2-5:80-100:28-32:28-32:2-5.

*Angelica sinensis, Panax notoginseng, Carthamus tinctorius* L., Lumbricus, Pearl, Borneol, *Astragalus membranaceus, Psoralen, Polygala tenuifolia* and *Radix glycyrrhizae* at the ratio of 200:60:15:90:3:3:90:30:30:3 are preferred.

The processing method of the dietary supplement mentioned herein is to powder all raw materials, screen the powder with more 80 meshes, and then made into decoction, powder, pill, tablet or capsule.

The usage of the dietary supplement is to orally take 5-12 g every time, three times a day, for adults.

The processing and taking methods, safety and experimental method of the dietary supplement mentioned herein are the same as those of Embodiment 4.

The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
| --- | --- | --- | --- | --- |
| Slight Abnormality | 63 | 60 | 95.2 | 2 |
| Moderate Abnormality | 56 | 52 | 92.9 | 4 |
| Severe Abnormality | 38 | 34 | 89.5 | 7 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
| --- | --- | --- | --- | --- |
| Osteoporosis | 41 | 38 | 92.7 | 14 |
| Osteonecrosis | 36 | 33 | 91.7 | 28 |
| Nonunion of fracture | 52 | 51 | 98.1 | 10 |
| Fibrous dysplasia | 36 | 33 | 91.7 | 26 |
| Bone cyst | 40 | 37 | 92.5 | 26 |
| Chondritis | 38 | 35 | 92.1 | 18 |

It indicates that this product has a good repair and improvement effect on multiple types of bone tissue decay, which is superior to that of Embodiment 1.

III. The experimental results of the population with muscle tissue decay are shown in the following table:

| Type | Total Number (Person) | Recovery Number (Person) | Recovery Rate (%) | Average Duration of Medication (Week) |
| --- | --- | --- | --- | --- |
| Recurrent sores | 49 | 45 | 91.8 | 13 |
| Unhealed wounds | 42 | 40 | 95.2 | 6 |
| Unhealed fistula and fistulous tract | 48 | 46 | 95.8 | 18 |
| Degenerative arthritis | 36 | 34 | 94.4 | 18 |
| Rheumatoid arthritis | 48 | 44 | 91.7 | 28 |

It indicates that this product has a good repair and improvement effect on various types of muscle tissue decay.

Embodiment 11

*Achyranthes bidentata, Sealwort, Paeonia lactiflora* Pall and *Eurycoma longifolia* are further included in the raw materials *Angelica sinensis, Panax notoginseng* and *Carthamus tinctorius* L., to form a reinforced formula, with *Angelica sinensis, Panax notoginseng, Carthamus tinctorius* L., *Achyranthes bidentata, Sealwort, Paeonia lactiflora* Pall and *Eurycoma longifolia* at the ratio of 180-220:55-65:12-18:28-32:28-32: 80-100:2-5. *Angelica sinensis, Panax notoginseng, Carthamus tinctorius* L., *Achyranthes bidentata, Sealwort, Paeonia lactiflora* Pall and *Eurycoma longifolia* at the ratio of 200:60:15:30:30:90:3 are preferred.

Introduction to Newly Further Included Raw Materials:

*Achyranthes bidentata* (Latin name: *Achyranthes bidentata* Blume.), also known as Hyssop, is a perennial herb of Genus Hyssop of Family Amaranthaceae.

*Achyranthes bidentata* (Scientific name: *Polygonatum sibiricum*), also known as Chicken Head Yellow Essence, Yellow Chicken Vegetable, and Pen Tube Vegetable.

*Eurycoma longifolia* is a wild shrub in tropical rain forests around the equator in Southeast Asia. It belongs to Genus Euryalium of Family Simarubaceae of Sapindales Order. Its root has various effects.

The processing and taking methods, safety and experimental method of the dietary supplement mentioned herein are the same as those of Embodiment 4. The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
| --- | --- | --- | --- | --- |
| Slight Abnormality | 50 | 47 | 94.0 | 2 |
| Moderate Abnormality | 44 | 40 | 90.9 | 4 |
| Severe Abnormality | 38 | 33 | 86.8 | 7 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 44 | 39 | 88.6 | 14 |
| Osteonecrosis | 36 | 32 | 88.9 | 28 |
| Nonunion of fracture | 50 | 48 | 96.0 | 10 |
| Fibrous dysplasia | 36 | 32 | 88.9 | 26 |
| Bone cyst | 39 | 36 | 92.3 | 26 |
| Chondritis | 38 | 35 | 92.1 | 18 |

It indicates that this product has a good repair and improvement effect on various types of bone tissue decay.

III. The experimental results of the population with muscle tissue decay are shown in the following table:

| Type | Total Number (Person) | Recovery Number (Person) | Recovery Rate (%) | Average Duration of Medication (Week) |
|---|---|---|---|---|
| Recurrent sores | 46 | 41 | 89.1 | 13 |
| Unhealed wounds | 44 | 42 | 95.5 | 6 |
| Unhealed fistula and fistulous tract | 36 | 35 | 97.2 | 18 |
| Degenerative arthritis | 42 | 40 | 95.2 | 18 |
| Rheumatoid arthritis | 36 | 30 | 83.3 | 28 |

It indicates that this product has a good repair and improvement effect on various types of muscle tissue decay.

Embodiment 12

Lumbricus, Pearl, Borneol, *Achyranthes bidentata*, Sealwort, *Paeonia lactiflora* Pall and *Eurycoma longifolia* are further included in the raw materials *Angelica sinensis, Panax notoginseng* and *Carthamus tinctorius* L., to form a reinforced formula, with *Angelica sinensis, Panax notoginseng, Carthamus tinctorius* L., Lumbricus, Pearl, Borneol, *Achyranthes bidentata*, Sealwort, *Paeonia lactiflora* Pall and *Eurycoma longifolia* at the ratio of 180-220:55-65:12-18:80-100:2-5:2-5:28-32:28-32: 80-100:2-5.

*Angelica sinensis, Panax notoginseng, Carthamus tinctorius* L., Lumbricus, Pearl, Borneol, *Achyranthes bidentata*, Sealwort, *Paeonia lactiflora* Pall and *Eurycoma longifolia* at the ratio of 200:60:15:90:3:3:30:30:90:3 are preferred.

The processing and taking methods, safety and experimental method of the dietary supplement mentioned herein are the same as those of Embodiment 4.

The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
|---|---|---|---|---|
| Slight Abnormality | 56 | 54 | 96.4 | 2 |
| Moderate Abnormality | 54 | 51 | 94.4 | 4 |
| Severe Abnormality | 42 | 38 | 90.5 | 7 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 48 | 44 | 91.7 | 14 |
| Osteonecrosis | 38 | 36 | 94.7 | 28 |
| Nonunion of fracture | 62 | 61 | 98.4 | 10 |
| Fibrous dysplasia | 36 | 33 | 91.6 | 26 |
| Bone cyst | 42 | 40 | 95.2 | 26 |
| Chondritis | 38 | 36 | 94.7 | 18 |

It indicates that this product has a good repair and improvement effect on various types of bone tissue decay.

III. The experimental results of the population with muscle tissue decay are shown in the following table:

| Type | Total Number (Person) | Recovery Number (Person) | Recovery Rate (%) | Average Duration of Medication (Week) |
|---|---|---|---|---|
| Recurrent sores | 46 | 43 | 93.4 | 13 |
| Unhealed wounds | 48 | 47 | 97.9 | 6 |
| Unhealed fistula and fistulous tract | 46 | 45 | 97.8 | 18 |
| Degenerative arthritis | 46 | 44 | 95.7 | 18 |
| Rheumatoid arthritis | 38 | 33 | 86.8 | 28 |

It indicates that this product has a good repair and improvement effect on various types of muscle tissue decay.

Embodiment 13

*Ligusticum wallichii, Rehmannia glutinosa, Eucommia ulmoides* and *Rhodiola rosea* are further included in the raw materials *Angelica sinensis, Panax notoginseng* and *Carthamus tinctorius* L., to form a reinforced formula, with *Angelica sinensis, Panax notoginseng, Carthamus tinctorius* L., *Ligusticum wallichii, Rehmannia glutinosa, Eucommia ulmoides* and *Rhodiola rosea* at the ratio of 180-220:55-65:12-18:80-100:28-32:28-32:2-5.

*Angelica sinensis, Panax notoginseng, Carthamus tinctorius* L., *Ligusticum wallichii, Rehmannia glutinosa, Eucommia ulmoides* and *Rhodiola rosea* at the ratio of 200:60:15:90:30:30:3 are preferred.

Introduction to Newly Further Included Raw Materials:
*Rehmannia glutinosa* is the earthnut of *Rehmannia Glutinosa* (Latin name:Chinese Foxglove), also known as Prepared *Rehmannia* or Foxglove.

*Eucommia ulmoides* (Scientific name: *Eucommia ulmoides* Oliver), also known as Bakelite, is a plant of Family Eucommiaceae. Its dry bark is used as medicine.

*Rhodiola rosea* (Scientific name: *Rhodiola rosea* L.), with the alias of Rose *Rhodiola rosea* and Saul Mapur (Tibetan name), is a perennial herb of Family Crassulaceae of Order Rrosaceae.

The processing and taking methods, safety and experimental method of the dietary supplement mentioned herein are the same as those of Embodiment 4.

The following are the experimental results of three applications:

I. The experimental situations of the weak population are as follows:

| Microcirculation Index | Total Number (Person) | Recovery Number (Person) | Overall Response Rate (ORR) (%) | Average Duration of Medication (Week) |
|---|---|---|---|---|
| Slight Abnormality | 55 | 53 | 96.4 | 3 |
| Moderate Abnormality | 44 | 41 | 93.2 | 5 |
| Severe Abnormality | 39 | 34 | 87.2 | 8 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 45 | 41 | 91.1 | 14 |
| Osteonecrosis | 40 | 37 | 92.5 | 28 |
| Nonunion of fracture | 46 | 45 | 97.8 | 10 |
| Fibrous dysplasia | 42 | 39 | 92.9 | 26 |
| Bone cyst | 38 | 36 | 94.7 | 26 |
| Chondritis | 36 | 34 | 94.4 | 18 |

It indicates that this product has a good repair and improvement effect on multiple types of bone tissue decay, which is superior to that of Embodiment 1.

III. The experimental results of the population with muscle tissue decay are shown in the following table:

| Type | Total Number (Person) | Recovery Number (Person) | Recovery Rate (%) | Average Duration of Medication (Week) |
|---|---|---|---|---|
| Recurrent sores | 56 | 52 | 92.9 | 13 |
| Unhealed wounds | 54 | 51 | 94.4 | 6 |
| Unhealed fistula and fistulous tract | 36 | 35 | 97.2 | 18 |
| Degenerative arthritis | 42 | 40 | 95.2 | 18 |
| Rheumatoid arthritis | 46 | 40 | 87.0 | 28 |

It indicates that this product has a good repair and improvement effect on various types of muscle tissue decay.

Embodiment 14

Lumbricus, Pearl, Borneol, *Ligusticum wallichii, Rehmannia glutinosa, Eucommia ulmoides* and *Rhodiola rosea* are further included in the raw materials, to form a reinforced formula with *Angelica sinensis, Panax notoginseng, Carthamus tinctorius* L., Lumbricus, Pearl, Borneol, *Ligusticum wallichii, Rehmannia glutinosa, Eucommia ulmoides* and *Rhodiola rosea* at the ratio of 180-220:55-65:12-18:80-100:2-5:2-5:80-100:28-32:28-32:2-5.

*Angelica sinensis, Panax notoginseng, Carthamus tinctorius* L., Lumbricus, Pearl, Borneol, *Ligusticum wallichii, Rehmannia glutinosa, Eucommia ulmoides* and *Rhodiola rosea* at the ratio of 200:60:15:90:3:3:90:30:30:3 are preferred.

The processing and taking methods, safety and experimental method of the dietary supplement mentioned herein are the same as those of Embodiment 4.

The following are the experimental results of the three applications:

I. The experimental situations of the weak population are as follows:

| Microcirculation Index | Total Number (Person) | Recovery Number (Person) | Overall Response Rate (ORR) (%) | Average Duration of Medication (Week) |
|---|---|---|---|---|
| Slight Abnormality | 58 | 57 | 98.3 | 3 |
| Moderate Abnormality | 54 | 52 | 96.3 | 5 |
| Severe Abnormality | 38 | 34 | 89.5 | 8 |

It indicates that this product has a good repair and improvement effect on a variety of microcirculation disturbance.

II. The experimental results of the population with bone tissue injury are shown in the following table:

| Type | Total Number (Person) | Recovery Number (Person) | Recovery Rate (%) | Average Duration of Medication (Week) |
|---|---|---|---|---|
| Osteoporosis | 55 | 52 | 94.5 | 14 |
| Osteonecrosis | 60 | 57 | 95.0 | 28 |
| Nonunion of fracture | 66 | 65 | 98.5 | 10 |
| Fibrous dysplasia | 52 | 49 | 94.2 | 26 |
| Bone cyst | 49 | 47 | 95.9 | 26 |
| Chondritis | 46 | 44 | 95.6 | 18 |

It indicates that this product has a good repair and improvement effect on multiple types of bone tissue decay, which is superior to that of Embodiment 1.

III. The experimental results of the population with muscle tissue decay are shown in the following table:

| Type | Total Number (Person) | Recovery Number (Person) | Recovery Rate (%) | Average Duration of Medication (Week) |
|---|---|---|---|---|
| Recurrent sores | 55 | 52 | 94.5 | 13 |
| Unhealed wounds | 58 | 56 | 96.6 | 6 |
| Unhealed fistula and fistulous tract | 62 | 61 | 98.4 | 18 |
| Degenerative arthritis | 52 | 50 | 96.2 | 18 |
| Rheumatoid arthritis | 48 | 43 | 89.6 | 28 |

It indicates that this product has a good repair and improvement effect on various types of muscle tissue decay.

What is claimed is:

1. A method for improving blood circulation and strengthening bone and muscle by administrating a Bone-Strengthening Pill (BSP) to a subject in need thereof, wherein the BSP comprises therapeutically effective amounts of decoctions of (i) *Angelica sinensis, Panax notoginseng* and *Carthamus tinctorius* L. or (ii) *Angelica sinensis, Panax notoginseng, Carthamus tinctorius* L., *Paeonia lactiflora* Pall, *Ligusticum wallichii, Polyqala tenuifolia* and *Panax quinquefolius*.

2. The method according to claim 1, wherein the ratio of the decoctions of (i) is *Angelico sinensis:Panax notoginsen-* g:*Carthamus linclorius* L. is 280-320: 55-65:12-18 by weight; and wherein the ratio of the decoctions of (ii) is *Angelica sinensis:Panax notoginseng:Carthamus tinctorius* L.: *Paeonia lactiflora* Pall:: *Ligusticum wallichii:Polvgala tenuifolia:Panax quinquefolius* is 280-320: 55-65 12-18: 80-100:25-35: 25-35 2-5 by weight.

* * * * *